US008022038B2

(12) United States Patent
Miyata et al.

(10) Patent No.: US 8,022,038 B2
(45) Date of Patent: Sep. 20, 2011

(54) COMPOSITION FOR ACCELERATION OF TYPE I COLLAGEN PRODUCTION

(75) Inventors: Satoshi Miyata, Yokohama (JP); Yukari Umino, Yokohama (JP)

(73) Assignee: Fancl Corporation, Kanagawa (JP)

( * ) Notice: Subject to any disclaimer, the term of this patent is extended or adjusted under 35 U.S.C. 154(b) by 368 days.

(21) Appl. No.: 12/088,655

(22) PCT Filed: Jul. 20, 2006

(86) PCT No.: PCT/JP2006/314393
§ 371 (c)(1),
(2), (4) Date: Mar. 28, 2008

(87) PCT Pub. No.: WO2007/037060
PCT Pub. Date: Apr. 5, 2007

(65) Prior Publication Data
US 2009/0325885 A1    Dec. 31, 2009

(30) Foreign Application Priority Data
Sep. 29, 2005   (JP) ................. 2005-283271

(51) Int. Cl.
A61K 38/06    (2006.01)
A61K 38/17    (2006.01)
A61K 38/39    (2006.01)

(52) U.S. Cl. ............... 514/17.2; 514/21.9; 530/356

(58) Field of Classification Search .............. None
See application file for complete search history.

(56) References Cited

U.S. PATENT DOCUMENTS

| 4,804,745 | A   |   | 2/1989  | Koepff et al. |         |
|-----------|-----|---|---------|---------------|---------|
| 5,529,769 | A   | * | 6/1996  | Cho et al.    | 424/74  |
| 6,699,900 | B2  | * | 3/2004  | Zielinski     | 514/452 |

FOREIGN PATENT DOCUMENTS

| JP | 52-111600       | 9/1977  |
| JP | 57-064688       | 4/1982  |
| JP | 62-223106       | 10/1987 |
| JP | 63-41396        | 2/1988  |
| JP | 01-100132       | 4/1989  |
| JP | 05-009406       | 1/1993  |
| JP | 05-286864       | 11/1993 |
| JP | 06-046875       | 2/1994  |
| JP | 06-504282       | 5/1994  |
| JP | 07-082299       | 3/1995  |
| JP | 07-196534       | 8/1995  |
| JP | 07-278012       | 10/1995 |
| JP | 2000-169328     | 6/2000  |
| JP | 2000-169332     | 6/2000  |
| JP | 2000-309521     | 11/2000 |
| JP | 2001-131084     | 5/2001  |
| JP | 2002-173424     | 6/2002  |
| JP | 2002-220333     | 8/2002  |
| JP | 2002-255448     | 9/2002  |
| JP | 2002-255847     | 9/2002  |
| JP | 2003-277399     | 10/2003 |
| JP | 2004-091397     | 3/2004  |
| WO | WO 2004/085429 A1 | 10/2004 |
| WO | WO 2005/048968 A1 | 6/2005  |

OTHER PUBLICATIONS

J. Scala, et al., "Effect of Daily Gelatine ingestion on Human Scalp Hair," Nutrition Reports International, vol. 13, No. 6, Jun. 1976, pp. 579-592.
W. Buckzko, et al., "Biological Effects of Degradation Products of Collagen by Bacterial Collagenase," Br. J. Pharmac., 69, pp. 551-554, 1980.
Y. Nagai, "Collagenase Digestion of Collagen," The Journal of Biochemistry, vol. 50, No. 6, pp. 486-492, 1961.
K. Katayama, et al., "A Pentapeptide from Type I Procollagen Promotes Extracellular Matrix Production," J. Bio. Chem., 268 (14), pp. 9941-9944, 1993.
N.I. Veretennikova, "Rigin, Another Phagocytosis-Stimulating Tetrapeptide Isolated From Human IgG," Int. J. Peptide Proten Res. 17, pp. 430-435, 1981.
J. Varani, et al., "All-Trans Retinoic Acid Stimulates Growth and Extracellular Matrix Production in Growth-Inhibited Cultured Human Skin Fibroblasts," J. Invest. Dermatol., vol. 94, No. 5, pp. 717-723, 1990.
J. Varani, et al., "Vitamin a Antagonizes Decreased Cell Growth and Elevated Collagen-Degrading Matrix Metalloproteinases and Stimulates Collagen Accumulation in Naturally Aged Human Skin," J. Invest. Dermatol., 116, pp. 480-486, 2000.
C.C. Zouboulis, "Retinoids: Is there a New Approach?" IFSCC Magazine vol. 3, No. 3, 2000.
Quercia, V., et al., "Proceedings of the 1st International Symposium on Chromatography in Biochemistry, Medicine and Environmental Research," Frigerio A. (Ed)., Elsevier Scientific Publishing Company, Amsterdam, Analytical Chemistry Symposia Series vol. 13, 1983.
G. Tittel, et al., "Hochleistungsflüssigchromatographie von Silymarin; II. Quantitative Bestimmung von Silymarin Aus *Silybum Marianum* Durch Hochleistungsflüssigchromatographie," Journal of Chromatography, 153, pp. 227-232, 1978. O.H. Lowry, et al., "Protein Measurement with the Folin Phenol Reagent," J. Biol. Chem., 193, pp. 265-275, 1951.
M.J. Bartek, "Skin Permeability in Vivo: Comparison in Rat, Rabbit, Pig and Man," The Journal of Invenstigative Dermatology, vol. 58, No. 3, pp. 114-123, 1972.
S. Kitajima, et al., "Identification of the active flavonolignan in silymarin to prevent skin aging," Seikagaku, vol. 77, No. 8, p. 968, 3P-591, Aug. 25, 2005.
K. Katayama, et al.,"A Pentapeptide from Type I Procollagen Promotes Extracellular Matrix Production," The Journal of Biological Chemistry, vol. 268, No. 14, pp. 9941-9944, 1993.
N.I. Veretennikova, et al., "Rigin, Another Phagocytosis-Stimulating Tetrapeptide Isolated From Human IgG.," Int. J. Peptide Protein Res. 17, pp. 430-435, 1981.
Akio Odera, "Hormon-yo Sayo no Aru Shinki Koroka Keshohin Genryo," Fragrance Journal, vol. 32, No. 8, pp. 94-98, 2004.
Maquart, et al., Glycyl-L-Histidyl-L-Lysine, a Triplet from the α2 (I) Chain of Human Type I Collagen, Stimulates Collagen Synthesis by Fibroblast Cultures, Annals of New York Academy of Sciences, vol. 580, 1990, p. 573-575.
Wagner, H., et al., Arznein. Forsch, 24, 266, 1974.
Tittel, G., et al., Journal of Chromatography, 135 (1977) 499-501.
Miyata, S., Silymarin, Geriatric Medicine vol. 42 No. 8, pp. 1037-1041, (2004).
* cited by examiner

*Primary Examiner* — Robert Landsman
*Assistant Examiner* — Ian Dang
(74) *Attorney, Agent, or Firm* — Knobbe Martens Olson & Bear LLP (57) ABSTRACT

It is an object of the present invention to provide a composition for promoting the production of type I collagen by human skin fibroblasts, and the present invention relates to a composition for promoting type I collagen production containing silybin and a peptide that promotes collagen production (peptide having an amino acid sequence of Gly-Pro-Hyp, Gly-His-Lys, Lys-Thr-Thr-Lys-Ser (SEQ ID NO: 1) or Gly-Glu-Pro-Arg (SEQ ID NO: 2).

8 Claims, 5 Drawing Sheets

SEQUENCE LISTING

<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

```
Lys Thr Thr Lys Ser
1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Glu Pro Arg
1
```

COMPOSITION FOR ACCELERATION OF TYPE I COLLAGEN PRODUCTION

This application is the U.S. National Phase under 35 U.S.C. §371 of International Application PCT/JP2006/314393, filed Jul. 20, 2006, which claims priority to Japanese Patent Application No. 2005-283271, filed Sep. 29, 2005. The International Application was published under PCT Article 21(2) in a language other than English.

TECHNICAL FIELD

The present invention relates to a composition having the effect of promoting the production of type I collagen by human skin fibroblasts.

PRIOR ART

Collagen accounts for approx. one-third of all protein produced in the body. It is found in large quantities in the blood vessel, skin and bone and plays an important function in the formation and building of blood vessel/skin/bone tissues as a cell scaffold. Collagen was long considered a type of protein offering low nutritional value because it is hardly broken down by digestive enzymes. However, people are having a second look at the effectiveness of collagen nowadays after the publication of reports suggesting that ingesting collagen promotes metabolism (Patent Literature 1) or hair growth (Non-patent Literature 1) and that collagen can be utilized as an arthropathy treatment drug (Patent Literature 2). Since collagen decreases with age, it is also considered that a reduction in collagen is a cause of weakening of blood vessels, loss of elasticity and flexibility of skin, and formation of lines and sagging.

Gelatin, which is a thermally denatured form of collagen, is utilized as an additive to improve the texture of food or in the production of cosmetics because of its high viscosity, coagulation property and moisture-keeping property (Patent Literature 3). However, unprocessed collagen and gelatin have high viscosity and are easy to coagulate, and thus in many cases collagen and gelatin are partially hydrolyzed before use. Being a protein, collagen also has antigenicity and therefore ingesting collagen presents a problem in people with allergy. For this reason, converting collagen into a low-molecular-weight form having no antigenicity by means of collagenase for use as a source of protein or fluid infusion component for allergic patients is reported (Patent Literature 4). As for the bioactivities of collagen decomposition products obtained through collagenase, such collagen decomposition products are known to have fibrin coagulation inhibition activity (Patent Literature 5) and anesthetic action (Non-patent Literature 2). There is also a report that collagen decomposition products obtained through *Clostridium histolyticum*-derived collagenase have 36% of their tripeptide content constituted by Gly-Pro-Hyp, which is the highest Gly-Pro-Hyp ratio found in all substances (Non-patent Literature 3).

An attempt has been made to use a collagen decomposition product containing Gly-Pro-Hyp, obtained through collagenase, as an effective ingredient in external drugs for skin and other products designed to prevent skin aging (Patent Literature 6).

Also, a biocollagen promoter has been developed that contains a collagen decomposition product containing Gly-Pro-Hyp, obtained through collagenase, especially such collagen decomposition product with a molecular weight of 400 or less (Patent Literature 7). A collagen decomposition product obtained through collagenase is assumed to promote collagen synthesis by acting as a material for biocollagen. In addition, peptides that promote collagen production have been developed, including Lys-Thr-Thr-Lys-Ser (SEQ ID NO: 1) being a pentapeptide derived from an α1 collagen decomposition product (Non-patent Literature 4), Gly-His-Lys being a tripeptide derived from an α2 collagen decomposition product (Non-patent Literature 5), and Gly-Glu-Pro-Arg (SEQ ID NO: 2) being a pentapeptide derived from an immunoglobulin G decomposition product (Non-patent Literature 6).

On the other hand, compositions have been discovered that promote the production of collagen not by acting as a material for biocollagen. For example, retinoic acid and its derivative retinol (Non-patent Literature 7), as well as silymarin which is a component derived from milk thistle extract (Patent Literature 8), have been developed. In addition, retinoic acid and its derivative retinol (Non-patent Literature 8) and silymarin derived from milk thistle extract (Patent Literature 9) have been shown to also suppress collagenase, which is a collagen decomposition enzyme.

Retinoic acid and its derivative retinol are not suitable for use in practical applications because they cause skin irritation and present other safety issues (Non-patent Literature 9) and are also unstable.

As explained above, various components and compositions have been developed that increase biocollagen. However, none of them have been proven to ensure safety and also demonstrate sufficient effects.

The present invention was developed based on the discovery that a combined use of silybin and various peptides would promote the production of type I collagen synergistically compared to when they are used alone.

Patent Literature 1: Japanese Patent Laid-open No. Hei 7-278012
Patent Literature 2: Japanese Patent Laid-open No. Sho 63-39821
Patent Literature 3: Japanese Patent Laid-open No. Sho 52-111600
Patent Literature 4: Japanese Patent Laid-open No. Hei 7-82299
Patent Literature 5: Japanese Patent Laid-open No. Hei 6-46875
Patent Literature 6: Japanese Patent No. 3504205
Patent Literature 7: Japanese Patent Laid-open No. 2001-1310844
Patent Literature 8: WO2004/085429
Patent Literature 9: Japanese Patent Laid-open No. 2002-173424
Patent Literature 10: Japanese Patent Laid-open No. Hei 5-286864
Patent Literature 11: Japanese Patent No. 2948818
Patent Literature 12: Japanese Patent Laid-open No. 2000-169328
Patent Literature 13: Japanese Patent Laid-open No. 2000-169332
Patent Literature 14: Japanese Patent Application No. 2002-255448
Patent Literature 15: Examined Japanese Patent Laid-open No. Hei 5-9406
Patent Literature 16: Examined Japanese Patent Laid-open No. Sho 63-41396
Patent Literature 17: Japanese Patent Laid-open No. 2002-255847
Non-patent Literature 1: Nutrition Reports International, 13, 579, 1976
Non-patent Literature 2: Br. J. Pharmacol., 69, 551, 1980
Non-patent Literature 3: J. Biochem., 50, 486, 1961

Non-patent Literature 4: J. Biol. Chem., 268 (14), 9941-9944, 1993

Non-patent Literature 5: Ann. NY Acad. Sci., 580, p 573

Non-patent Literature 6: Int J Pept Protein Res., 17 (4), p 430-435., 1981

Non-patent Literature 7: J. Invest. Dermatol., Vol. 94, No. 5, p 717-723, 1990

Non-patent Literature 8: Varani J., et al., J. Invest. Dermatol., 116, 480-486, 2000

Non-patent Literature 9: Zouboulis, C. C., Retinoids: is there a New Approach?, IFSCC Magazine, Vol. 3, No. 3, 2000

Non-patent Literature 10: Wagner, H., et al., Arznein. Forsch, 24, 466, 1974.

Non-patent Literature 11: Tittel, G., et al., J. Chromatogr., 135, 499, 1977.

Non-patent Literature 12: Tittel, G., et al., J. Chromatogr., 153, 227, 1978.

Non-patent Literature 13: Quercia, V., et al., J. Chromatography in Biochemistry, Medicine and Environmental Research, Frigerio A. (Ed)., ElsevierScientific Publishing Company, Amsterdam, 1983, p 1.

Non-patent Literature 14: Lowry, O et. al., J. Biol. Chem., 193, 265, 1951

Non-patent Literature 15: M. J. Barttek, et al., J. Invest. Dermatol., 58, 114, 1972

SUMMARY OF THE INVENTION

Problems to be Solved by the Invention

It is an object of the present invention to provide a composition for promoting the production of type I collagen by human skin fibroblasts.

Means for Solving the Problems

The inventors examined ways to enhance the production of type I collagen more effectively.

As a result, it was found that a combined use of a collagen-derived peptide that promotes collagen production by acting as a material for collagen, and silybin, would promote the production of type I collagen synergistically, the discovery of which led to the development of the present invention.

In other words, the present invention relates to the following: (1) a composition for promoting type I collagen production, containing silybin and a peptide that promotes collagen production; (2) a composition according to an embodiment, wherein the peptide that promotes collagen production comprises one or two or more types selected from peptides having an amino acid sequence of Gly-Pro-Hyp, Gly-His-Lys, Lys-Thr-Thr-Lys-Ser (SEQ ID NO: 1) or Gly-Glu-Pro-Arg (SEQ ID NO: 2); (3) a composition according to any one of Claims 1 to 4, used for the purpose of preventing and/or improving lines, sagging, dull complexion and pigmentation of skin; (4) a cosmetic containing silybin and one or two or more types selected from peptides having an amino acid sequence of Gly-Pro-Hyp, Gly-His-Lys, Lys-Thr-Thr-Lys-Ser (SEQ ID NO: 1) or Gly-Glu-Pro-Arg; (SEQ ID NO: 2) (5) a food containing silybin and one or two or more types selected from peptides having an amino acid sequence of Gly-Pro-Hyp, Gly-His-Lys, Lys-Thr-Thr-Lys-Ser (SEQ ID NO: 1) or Gly-Glu-Pro-Arg (SEQ ID NO: 2); and (6) a composition according to an embodiment for animals.

EFFECTS OF THE INVENTION

A composition having an excellent effect in promoting type I collagen production by human skin fibroblasts was provided by using silybin in combination with a peptide that promotes collagen production.

Application of a composition conforming to the present invention as a cosmetic, or ingestion of such composition as a food, is expected to improve the resilience and elasticity of skin and thereby prevent and/or improve lines and sagging of skin.

Compositions conforming to the present invention are also safe to skin.

BEST MODE FOR CARRYING OUT THE INVENTION

Silymarin (CAS No. 65666-07-1) is a general term for flavonolignans extracted from milk thistle of the Compositae family (scientific name: *Silybum marianum* Gaertn; other names: Mary thistle, cotton thistle; CAS No. 84604-20-6), and expressed by the molecular formula $C_{25}H_{22}O_{10}$. It is a composition that contains silybin (CAS No. 22888-70-6), silydianin (CAS No. 29782-68-1), silychristin (CAS No. 33889-69-9), isosilybin (CAS No. 72581-71-6), etc. (Non-patent Literature 10). Under the present invention, compositions that contain these flavonolignans contained in milk thistle extract are collectively referred to as silymarin, as is done in the prior art. Also, silymarin is a mixture of flavonolignans, as mentioned above, and the content of silymarin in a plant extract or plant can be measured using any method based on spectrophotometry (Non-patent Literature 11), method using thin-layer chromatography (Non-patent Literature 9), or method using high-speed liquid chromatography (Non-patent Literatures 12 to 14). Among these measurement methods, 2,4-dinitrohydrazine analysis, which is a method based on spectrophotometry, is reported in the German Pharmacopeia (monograph relating to *Silybum marianum* fruit) and widely used.

Accordingly, the 2,4-dinitrohydrazine analysis method is used to quantify compositions constituted by a mixture of the aforementioned ingredients where, specifically, quantities are indicated by equivalent silybin percentages by mass.

In Europe, silymarin has been used since ancient times for the purpose of preventing and treating liver diseases. Silymarin is also widely known as an anti-oxidant. Silymarin is known as a composition having beneficial effects on skin and the known beneficial effects of silymarin include a utility as a treatment drug for psoriasis and atopic dermatitis (Patent Literature 10), utility as a composition containing a flavonolignan and phospholipid complex as its active ingredient and therefore useful in the treatment of erythema, burns, dystrophy of skin or viscous membrane and dermatitis, prevention of skin aging, and protection of skin against external irritations such as radioactive ray, wind and sunlight (Patent Literature 11), utility as an agent to enhance the skin's permeation-blocking barrier property (Patent Literature 12), utility as an agent to suppress sebum secretion (Patent Literature 13), utility as a composition to prevent aging of skin by preventing and improving flattening of epidermis (Patent Literature 14), utility as a cosmetic to prevent aging of skin by exhibiting an anti-oxidative property (Patent Literature 15), and action to promote type I collagen production by human skin fibroblasts and in three-dimensional skin models (Patent Literature 8), among others.

As ways to isolate silymarin from milk thistle fruit at high purity, a method to isolate silymarin with a purity of 70 to 80% and a method to isolate silymarin with a purity of 90 to 96% (Patent Literature 16) have been reported. Silymarin is normally extracted from milk thistle seed using ethanol, ethyl acetate, acetone, etc., and is sold commercially as an extract material in the form of dry powder produced by spray-drying an extract. As for silybin used under the present invention, any silybin contained in any such silymarin prepared and sold commercially in this manner can be used directly. It is also possible to use a concentrated extract of silybin from milk thistle, or any compound produced by isolating and refining such extract can be used, as well.

Under the present invention, all parts of plants containing silybin can be used, including leaf, stem, sprout, flower, wooden part, bark and other parts that grow on the ground; root, tube and other parts that grow underground; as well as seed and resin.

Under the present invention, silybin and any plant containing silybin can be used in a dry form produced by drying each substance directly, or in a dissolved form produced by dissolving each substance in various solvents. For example, the above substances can be dissolved in water; ethanol, methanol and other alcohols; propylene glycol, 1,3-butylene glycol and other polyhydric alcohols; as well as ether, acetone, ethyl acetate and other organic solvents.

Under the present invention, silybin and any plant containing silybin can be naturally dried, dried by hot air, freeze-dried, or fermented and the obtained dried or fermented substance can be used directly. If a plant extract is to be prepared, the result obtained through extraction, concentration, pulverization or other process according to normal methods can be used.

Under the present invention, the peptide that promotes collagen production may preferably be a peptide having an amino acid sequence of Gly-Pro-Hyp, Gly-His-Lys, Lys-Thr-Thr-Lys-Ser (SEQ ID NO: 1) or Gly-Glu-Pro-Arg (SEQ ID NO: 2).

Gly-Pro-Hyp is a peptide composition obtained through specific decomposition of a collagen or gelatin component by collagenase, and is known to be digested and absorbed more quickly and efficiently compared to traditional collagen, gelatin or any hydrolyzate thereof (Patent Literature 17). As mentioned above, there is a report that collagen decomposition products obtained through *Clostridium histolyticum*-derived collagenase have 36% of their tripeptide content constituted by Gly-Pro-Hyp, which is the highest Gly-Pro-Hyp ratio found in all substances (Non-patent Literature 3), and this knowledge certainly provides an efficient method to produce Gly-Pro-Hyp. Under the present invention, Gly-Pro-Hyp may be chemically synthesized.

Under the present invention, Gly-His-Lys may be a product obtained by breaking down α2 procollagen using collagenase or other collagen decomposition enzyme. Gly-His-Lys can also be chemically synthesized.

Under the present invention, Lys-Thr-Thr-Lys-Ser (SEQ ID NO: 1) may be a product obtained by breaking down α1 procollagen using collagenase or other collagen decomposition enzyme. Lys-Thr-Thr-Lys-Ser (SEQ ID NO: 2) can also be chemically synthesized.

Under the present invention, Gly-Glu-Pro-Arg (SEQ ID NO: 2) may be a product obtained by breaking down immunoglobulin G using trypsin or other decomposition enzyme. Gly-Glu-Pro-Arg (SEQ ID NO: 1) can also be chemically synthesized.

A composition for promoting type I collagen production as proposed by the present invention promotes the production of type I collagen, which is a key protein constituting the extracellular matrix of dermis, and therefore improves the resilience and elasticity of skin, prevents and/or improves the formation of lines and sagging of skin caused by aging or exposure to ultraviolet (UV) light, and ultimately helps maintain youthful-looking skin.

A composition for promoting type I collagen production as proposed by the present invention can be manufactured as a cosmetic or other form of external drug for skin, or as a food.

In cosmetic applications, silybin, a source of silybin such as silymarin, or plant containing silybin or extract of such plant, and a peptide selected from Gly-Pro-Hyp, Gly-His-Lys, Lys-Thr-Thr-Lys-Ser (SEQ ID NO: 1) and Gly-Glu-Pro-Arg (SEQ ID NO: 2), can be combined and used directly as ingredients, or they can be added to wheat germ oil or olive oil, for use in the manufacture of a cosmetic.

In food applications, silybin, a source of silybin such as silymarin, or plant containing silybin or extract of such plant, and a peptide selected from Gly-Pro-Hyp, Gly-His-Lys, Lys-Thr-Thr-Lys-Ser (SEQ ID NO: 1) and Gly-Glu-Pro-Arg (SEQ ID NO: 1), can be combined and used directly as a food, or they can be mixed with various nutritional components to be made into a food or added to a desired food. For example, it is possible to add an appropriate auxiliary such as starch, milk sugar, maltose, vegetable oil powder, cacao powder or stearic acid, and then shape the mixture into an edible form, such as granule, pellet, tablet, capsule or paste, using a commonly used method to produce a health supplement, functional health food or the like. In addition, the aforementioned ingredients can also be added to various food products, such as ham, sausage and other processed meat products, fish cake and other processed seafood products, bread, confectionary, butter, powder milk and fermented milk products, or they can be added to water, fruit juice, milk, soda and other beverages.

The blending ratio (mol ratio) of silybin and various peptides in a composition for promoting type I collagen production as proposed by the present invention is not specifically limited, but it can instead be selected and determined as deemed appropriate according to the preparation method and dosage form of each component among other conditions. However, the blending ratio may preferably be 1 part of silybin and 2 to 6 parts of various peptides.

The effective content of silybin and that of a peptide that promotes collagen production in a composition, cosmetic or food for promoting type I collagen production as proposed by the present invention are not specifically limited, but they can instead be selected and determined as deemed appropriate according to the preparation method and dosage form of each component among other conditions. When the present invention is used for an external drug for skin, however, silybin and a peptide that promotes collagen production may preferably be contained by 0.01 to 2 percent by weight, respectively. When the present invention is used as a tablet, drink or other forms of food, on the other hand, they may preferably be contained by 0.1 to 10 percent by weight.

The effective application amount of a composition, cosmetic or food for promoting type I collagen production as proposed by the present invention can be determined as deemed necessary according to the application pathway, application schedule and dosage form among other conditions. For example, the amount can be adjusted as deemed appropriate in a range of 0.01 to 10 g per day and the entire amount may be taken at once or in portions over several times throughout a day.

In food applications, the present invention can be used directly or by mixing with various nutritional components. For example, it is possible to add an appropriate auxiliary such as starch, milk sugar, maltose, vegetable oil powder, cacao powder or stearic acid, and then shape the mixture into an edible form, such as granule, pellet, tablet, capsule or paste, using a commonly used method to produce a health supplement, functional health food or the like. In addition, the present invention can also be added to various food products, such as ham, sausage and other processed meat products, fish cake and other processed seafood products, bread, confectionary, butter, powder milk and fermented milk products, or it can be added to water, fruit juice, milk, soda and other beverages. Such agents and foods may be manufactured using preparation technologies that are normally employed.

In cosmetic applications, the present invention can be used directly as an ingredient, or added to wheat germ oil or olive oil, to be used in the manufacture of a cosmetic.

A parenteral composition can be applied in the form of liquid such as aqueous solution, oil solution, emulsion or suspension; in the form of semi-solid such as gel or cream; or in the form of solid such as powder, granule, capsule, microcapsule or solid. Any of these forms can be prepared using a known traditional method for use as a lotion, emulsion, gel, cream, ointment, plaster, poultice, aerosol, suppository, injection, powder or various other dosage forms. These can be spread, attached, sprayed or otherwise applied to the body. Among these dosage forms, lotion, emulsion, cream, ointment, plaster, poultice and aerosol are especially suitable as a form of external drug for skin. As for cosmetics, the present invention can be made into skin care products such as lotion, milky lotion, cream and mask; makeup products such as makeup base lotion, makeup cream, milky or cream-type or paste-type foundation, lipstick, eye color and cheek color; and body care products such as hand cream, leg cream and body lotion, among others.

For greater convenience, the present invention can be produced in the form of a composition mixed with an extender. Examples of substances that can be used as an extender include glucose, lactose, maltose, sucrose and other sugars; sorbitol and other sugar alcohols; dextrin, cyclodextrin and other processed starches; wheat starch, cornstarch and other starches; casein, soybean protein and other proteins; Arabian gum, sodium alginate, sodium caseinate, gelatin, pectin, powder cellulose, carboxymethyl cellulose and other polymer stabilizers; lecithin, sucrose fatty acid ester, propylene glycol fatty acid ester, glycerin fatty acid ester and other emulsifiers; and calcium powder, among others.

A composition, cosmetic or food for promoting type I collagen production as proposed by the present invention can contain a compound having an anti-oxidative action. This compound having an anti-oxidative action is not specifically limited, but examples include various vitamins, rutin and various other polyphenols, tocotrienol, coenzyme Q10 and natural components containing any of the foregoing.

A composition, cosmetic or food for promoting type I collagen production as proposed by the present invention can contain a component that promotes the removal of accumulated abnormal protein in the body. This component that promotes the removal of accumulated abnormal protein in the body is not specifically limited, but examples include soybean saponin, kale extract, *Bletilla striata* extract and *Iris sanguinea* extract, among others.

In addition to the above, other substances such as those listed below may be added according to the purpose and dosage form.

Examples of oils that can be used include, among others, camellia oil, evening primrose oil, *Macadamia* nut oil, olive oil, rape seed oil, corn oil, sesame oil, jojoba oil, germ oil, wheat germ oil, glycerin trioctate and other liquid oils; cacao oil, coconut oil, hardened coconut oil, palm oil, palm kernel oil, tallow oil, tallow kernel oil, hardened oil, hardened castor oil and other solid oils; and bees wax, candelilla wax, cotton wax, rice bran wax, lanolin, lanolin acetate, liquid lanolin, sugarcane wax and other waxes.

Examples of carbohydrates that can be used include, among others, liquid paraffin, squalene, squalane and micro crystalline wax.

Examples of higher fatty acids that can be used include, among others, lauric acid, myristic acid, palmitic acid, stearic acid, oleic acid, linoleic acid, linolenic acid, docosahexaenoic acid (DHA) and eicosa-pentaenoic acid (EPA).

Examples of higher alcohols that can be used include, among others, lauryl alcohol, stearyl alcohol, cetyl alcohol, cetostearyl alcohol and other straight-chain alcohols; and monostearyl glycerin ether, lanolin alcohol, cholesterol, phytosterol, octyl dodecanol and other branched-chain alcohols.

Examples of silicones that can be used include, among others, dimethyl polysiloxane, methyl phenyl polysiloxane and other chain polysiloxanes; and decamethyl cyclopentane siloxane and other cyclic polysiloxanes.

Examples of anionic surface active agents that can be used include, among others, sodium laurate and other fatty acid salts; sodium lauryl sulfate and other higher alkyl sulfuric ester salts; POE triethanol amine lauryl sulfate and other alkyl ether sulfuric ester salts; N-acyl sarcosinic acid; sulfosuccinic acid salt; and N-acyl amino acid salt.

Examples of cationic surface active agents that can be used include, among others, stearyl trimethyl ammonium chloride and other alkyl trimethyl ammonium salts; and benzalkonium chloride; and benzethonium chloride.

Examples of ampholytic surface active agents that can be used include, among others, alkyl betaine, amide betaine and other betaine surface active agents.

Examples of nonionic surface active agents that can be used include, among others, sorbitan monooleate and other sorbitan fatty acid esters; and hardened castor oil derivatives.

Examples of preservatives that can be used include, among others, methyl paraben and ethyl paraben.

Examples of sequestering agents that can be used include, among others, ethylene diamine disodium tetraacetate, edetic acid, sodium edetate salt and other edetic acid salts.

Examples of polymers that can be used include, among others, Arabian gum, tragacanth gum, galactan, guar gum, carrageenan, pectin, agar, quince seed, dextran, pullulan, carboxy methyl starch, collagen, casein, gelatin, methyl cellulose, methyl hydroxy propyl cellulose, hydroxy ethyl cellulose, carboxy methyl cellulose sodium (CMC), sodium alginate, carboxy vinyl polymers (CARBOPOL, etc.) and other vinyl polymers.

Examples of thickeners that can be used include, among others, carrageenan, tragacanth gum, quince seed, casein, dextrin, gelatin, CMC, hydroxy ethyl cellulose, hydroxy propyl cellulose, carboxy vinyl polymer, guar gum, xanthan gum and bentonite.

Examples of powder components that can be used include, among others, talc, kaolin, mica, silica, zeolite, polyethylene powder, polystyrene powder, cellulose powder, inorganic white pigments, inorganic red pigments, titanium oxide coated mica, titanium oxide coated talc, colored titanium oxide coated mica and other pearl pigments; and red 201, red 202 and other organic pigments.

Examples of UV absorbents that can be used include, among others, para-aminobenzoic acid, phenyl salicylate, isopropyl para-methoxy cinnamate, octyl para-methoxy cinnamate and 2,4-dihydroxy benzophenone.

Examples of UV blockers that can be used include, among others, titanium oxide, talc, carmine, bentonite, kaolin and zinc oxide.

Examples of moisture-keeping agents that can be used include, among others, polyethylene glycol, propylene glycol, dipropylene glycol, 1,3-butylene glycol, 1,2-pentane diol, glycerin, diglycerin, polyglycerin, xylitol, maltitol, maltose, sorbitol, glucose, fructose, sodium chondroitin sulfate, sodium hyaluronate, sodium lactate, pyrrolidone carboxylic acid and cyclodextrin.

Examples of medicinal components that can be used include, among others, various forms of vitamins including vitamin A oil, retinol and other forms of vitamin A; riboflavin and other forms of vitamin $B_2$; pyridoxine hydrochloride and other forms of vitamin $B_6$; L-ascorbic acid, L-ascorbic acid ester phosphate, L-ascorbic acid ester monopalmitate, L-ascorbic acid ester dipalmitate, L-ascorbic acid-2-glucoside and other forms of vitamin C; calcium pantothenate and other pantothenates; vitamin $D_2$, cholecalciferol and other forms of vitamin D; α-tocopherol, tocopherol acetate, nicotinic acid DL-α-tocopherol and other forms of vitamin E.

Other examples of substances that can be added include, among others, placenta extract, glutathione, *Saxifraga stolonifera* extract and other whitening agents; royal jelly, beech extract and other skin activators; capsaicin, zingherone, cantharides tincture, ichthammol, caffeine, tannic acid, γ-oryzanol and other blood-circulation promoters; glycyrrhizinic acid derivatives, glycyrrhetinic acid derivatives, azulene and other anti-inflammatory agents; arginine, serine, leucine, tryptophane and other amino acids; and maltose sucrose condensate, lysozyme chloride and other agents for controlling normal bacteria flora. Further examples of substances that can be added include, among others, chamomile extract, parsley extract, beech extract, wine yeast extract, grapefruit extract, Japanese honeysuckle extract, rice extract, grape extract, hop extract, rice bran extract, loquat extract, cork tree bark extract, *coix* seed extract, *swertia japonica* extract, melilot extract, birch extract, licorice extract, peony extract, soapwort extract, loofa extract, cayenne pepper extract, lemon extract, gentian root extract, *perilla* extract, aloe extract, rosemary extract, sage extract, thyme extract, tea extract, seaweed extract, cucumber extract, clove extract, carrot extract, horse chestnut extract, *hamamelis* extract, mulberry extract and various other extracts.

Next, the present invention is explained in further details using test examples and examples. It should be noted, however, that the present invention is not at all limited to these test examples and examples.

[Preparation of Agents]

An appropriate amount of a solution prepared by dissolving silybin (Sigma-Aldrich Corp.) in a dimethyl sulfoxide of biochemical reagent grade (DMSO; Wako Pure Chemical Industries, Ltd.) was added to a culture solution and this culture solution was used to treat a three-dimensional skin model.

An appropriate amount of a solution prepared by dissolving silymarin (Sigma-Aldrich Corp.) in a dimethyl sulfoxide of biochemical reagent grade (DMSO; Wako Pure Chemical Industries, Ltd.) was added to a culture solution and this culture solution was used to treat a three-dimensional skin model.

Silydianin and silychristin were fractionated using the following method. First, 2 g of silymarin (Sigma-Aldrich Corp.) was dissolved in 10 ml of ethanol, and then the mixture was fractionated using a 200-ml ODS column (DM1020T by Fuji Silysia Chemical Ltd.) under a solvent condition of 1 part of water to 1 part of methanol, to obtain sparse fractions of silydianin and silychristin.

The sparse fractions of silydianin and silychristin were respectively fractionated using a 200-ml silica gel chromatographic column under a solvent condition of 95 parts of chloroform to 5 parts of methanol, to obtain 17 mg of refined silychristin and 34 mg of refined silydianin. The obtained refined silychristin and silydianin were then dissolved in a dimethyl sulfoxide of biochemical reagent grade (DMSO; Wako Pure Chemical Industries, Ltd.), and an appropriate amount of each mixture was added to a culture solution and this culture solution was used to treat a three-dimensional skin model.

For Gly-Pro-Hyp, a commercial product was used (sold by Wako Pure Chemical Industries, Ltd., manufactured by Bachem AG in Switzerland).

Lys-Thr-Thr-Lys-Ser (SEQ ID NO: 1), Gly-His-Lys and Gly-Glu-Pro-Arg (SEQ ID NO: 2) were synthesized by Nikka Techno Service Co., Ltd. according to normal methods. The synthesized peptides were refined using reverse-phase HPLC. The purities of synthesized peptides were confirmed to have a purity of 90% or above based on amino acid analysis and purity analysis by reverse-phase HPLC. These peptides were dissolved in a dimethyl sulfoxide of biochemical reagent grade (DMSO; Wako Pure Chemical Industries, Ltd.), and an appropriate amount of each mixture was added to a culture solution and this culture solution was used to treat a three-dimensional skin model.

[Three-dimensional Human Skin Model]

Three-dimensional human skin models are widely used in safety evaluation and effectiveness evaluation as a simulated model of human skin. In this test, TESTSKIN (LSE-high) (Toyobo Co., Ltd.) was used as a three-dimensional human skin model.

[Preparation of Three-dimensional Human Skin Model Extract Sample Treated with Each Agent]

A culture medium was added to the outer well of TESTSKIN (LSE-high) and cultured for 24 hours. Thereafter, the culture solution was changed and each agent was added by 100 µl onto the tissues in the assay ring, after which the medium was cultured for 36 hours. Thereafter, the tissues were collected and a tissue extraction solution (50 mM Tris-HCl (pH 7.5), 0.5% (Octylphenoxy) polyethoxyethanol (Sigma-Aldrich Corp.)) was added, and then the mixture was homogenized using a homogenizer made of fluorocarbon resin. The homogenized mixture was centrifuged for 30 minutes at 10,000×G to remove tissue fragments, and then dialyzed overnight in distilled water at 4° C. Thereafter, the dialyzed mixture was freeze-dried to remove water. A tissue extraction solution was added to obtain a x20 concentrate, and this concentrate was used in Western blotting as a three-dimensional skin model extract sample.

[Evaluation of Action to Promote Type I Collagen Production by Western Blotting]

Using a three-dimensional human skin model extract sample, 10 µg of protein was applied per lane, after which the sample was separated via SDS-PAGE and the result was transferred onto nitrocellulose membranes. The transferred nitrocellulose membranes were soaked in a blocking solution (solution prepared by dissolving skim milk in a PBS containing 0.1% polyoxyethylene (20) sorbitan monolaurate to achieve a concentration of 5%) and blocked for one whole day at 4° C. The blocked membranes were washed with a washing solution (PBS containing 0.1% polyoxyethylene (20) sorbitan monolaurate) and then soaked in a primary antibody (polyclonal antibody of type I collagen (Rockland Inc.) adjusted to 500 ng/ml using a washing solution) to cause reaction for 1 hour at room temperature. The reacted membranes were washed and then soaked in a secondary antibody (horseradish peroxidase labeled anti-rabbit immunoglobulin G adjusted to 250 ng/ml using a washing solution) to cause reaction for 1 hour at room temperature. The reacted membranes were washed and then detection was performed using an ECL plus Western blotting detection reagent (Amersham Biosciences Inc.). The detected band was also scanned into an image scanner (Amersham Biosciences Inc.) and analyzed using image master software (Amersham Biosciences Inc.) for conversion to numerical values.

Example 1

Figure 1:
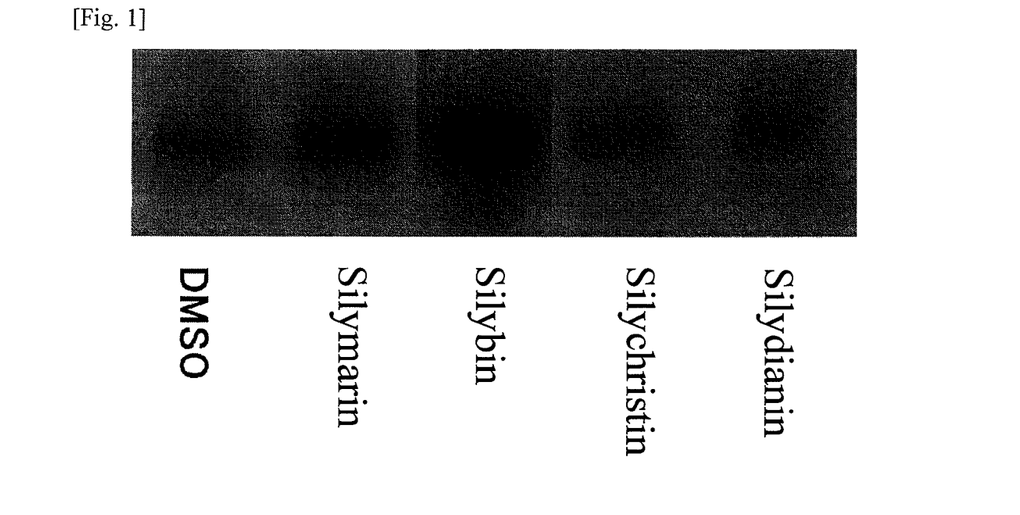
FIG. 1 A graph showing the detection results, by means of Western blotting, of the type I collagen production by silybin, silydianin and silychristin in a three-dimensional human skin model.

Evaluation of Effective Ingredient Contained in Silymarin, Involved in Promotion of Type I Collagen Production Three-dimensional human skin models were treated with 10 µg/ml of silymarin and also with silybin, silychristin and silydianin at a concentration of 10 µM, respectively, and the amount of type I collagen was measured by means of Western blotting. FIG. 1 shows the detected bands, while FIG. 2 shows a graph indicating the numerical values of detected bands.

Figure 2:
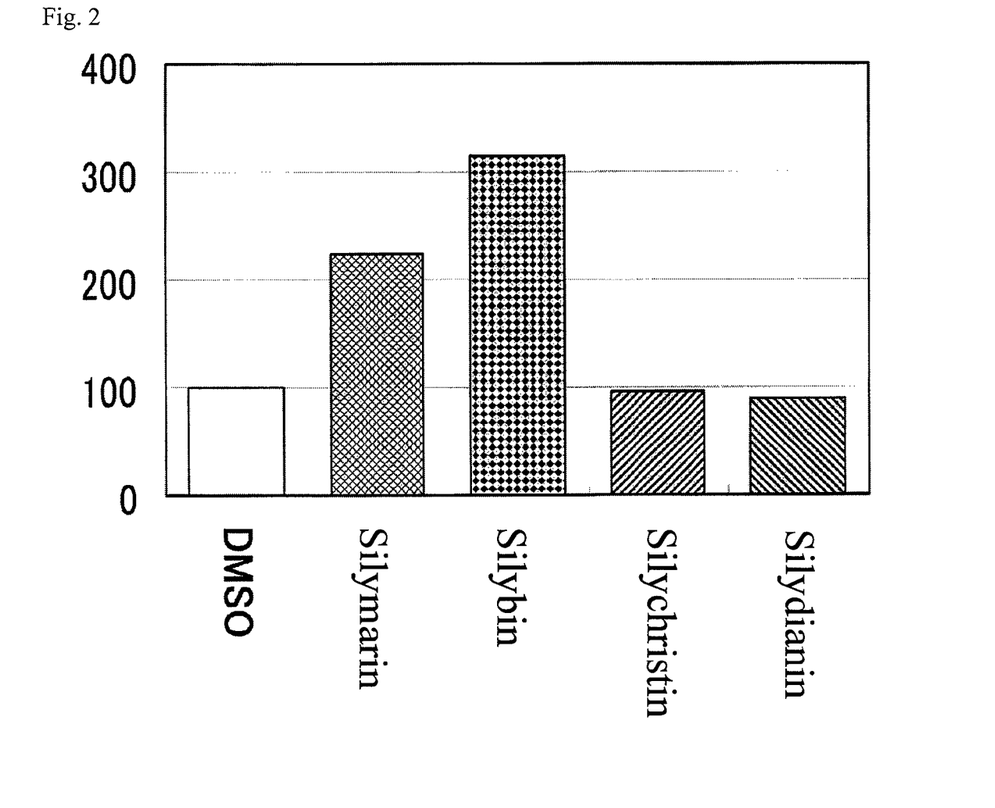
FIG. 2 A graph showing the numerical values of the results in FIG. 1, derived by conversion based on imaging analysis processing.

When treated with 10 µg/ml of silymarin, and with silybin, a component contained in silymarin, at 10 µM, production of type I collagen was promoted to 2.3 times and 3.2 times, respectively, compared to the level in the control that was not given any treatment (FIGS. 1 and 2). On the other hand, treating with silychristin and silydianin, both components contained in silymarin, at 10 µM, resulted in type I collagen production of 0.95 time and 0.9 time, respectively, compared to the level in the control that was not given any treatment (FIGS. 1 and 2). Accordingly, it is clear that silybin contained in silymarin is an effective ingredient involved in the promotion of type I collagen production.

Example 2

Figure 3:
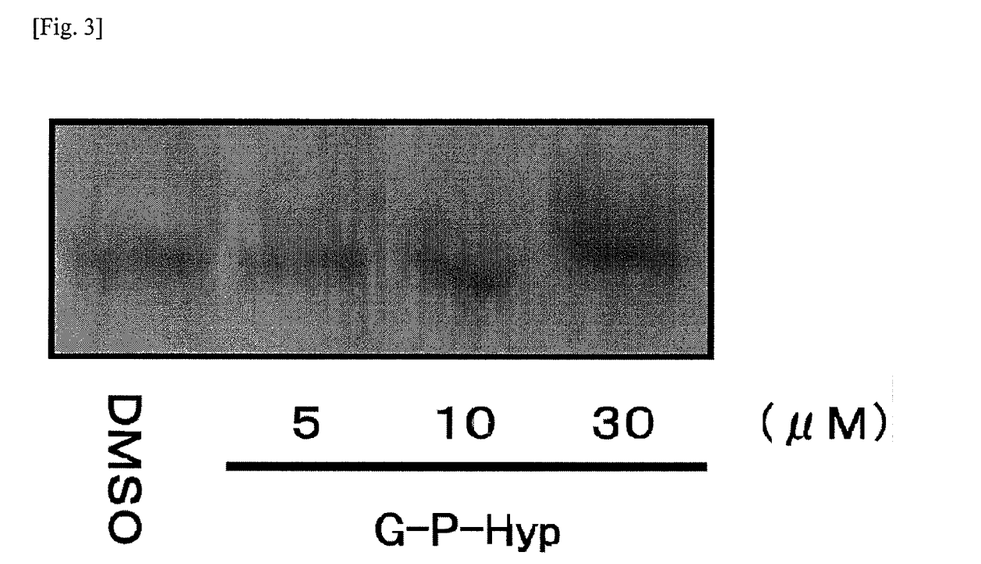
FIG. 3 A graph showing the detection results, by means of Western blotting, of the type I collagen production by a tripeptide having a Gly-Pro-Hyp (referred to as "G-P-Hyp") sequence in a three-dimensional human skin model.
Figure 4:
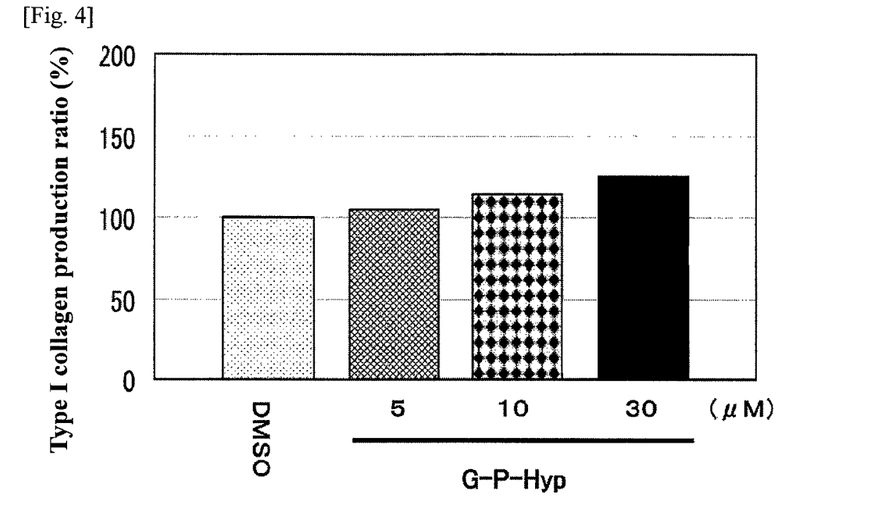
FIG. 4 A graph showing the numerical values of the results in FIG. 3, derived by conversion based on imaging analysis processing. Gly-Pro-Hyp is referred to as "G-P-Hyp."
Figure 5:
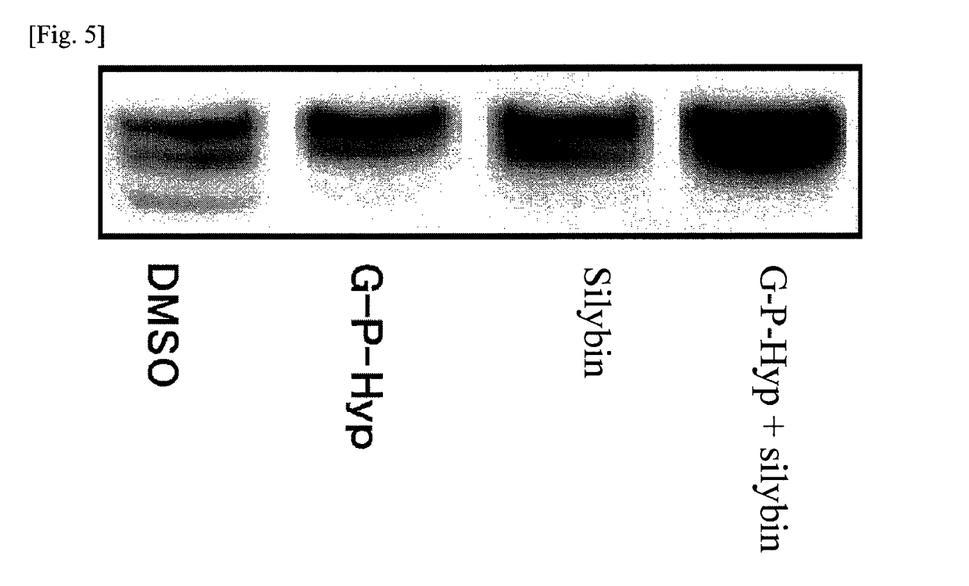
FIG. 5 A graph showing the detection results, by means of Western blotting, of the type I collagen production by a tripeptide having a Gly-Pro-Hyp (referred to as "G-P-Hyp") sequence and silybin in a three-dimensional human skin model.

Evaluation of Actions to Promote Type I Collagen Production from Use of Gly-Pro-Hyp Alone and Combined Use of Gly-Pro-Hyp with Silybin Three-dimensional human skin models were treated with Gly-Pro-Hyp at concentrations of 5, 10 and 30 µM, and the amount of type I collagen was measured by means of Western blotting. FIG. 3 shows the detected bands, while FIG. 4 shows a graph indicating the numerical values of detected bands. Similarly, measurement was performed when 30 µM of Gly-Pro-Hyp was used alone, 5 µM of silybin was used alone, and 30 µM of Gly-Pro-Hyp and 5 µM of silybin were used in combination. FIG. 5 shows the detected bands, while FIG. 6 shows a graph indicating the numerical values of detected bands.

Treating with Gly-Pro-Hyp at 5, 10 and 30 µM resulted in type I collagen production of 1.05 times, 1.15 times and 1.25 times, respectively, compared to the level in the control that was not given any treatment (FIGS. 3 and 4). Accordingly, it is clear that, although Gly-Pro-Hyp alone exhibits an action to promote type I collagen production, the action is not very strong.

Figure 6:
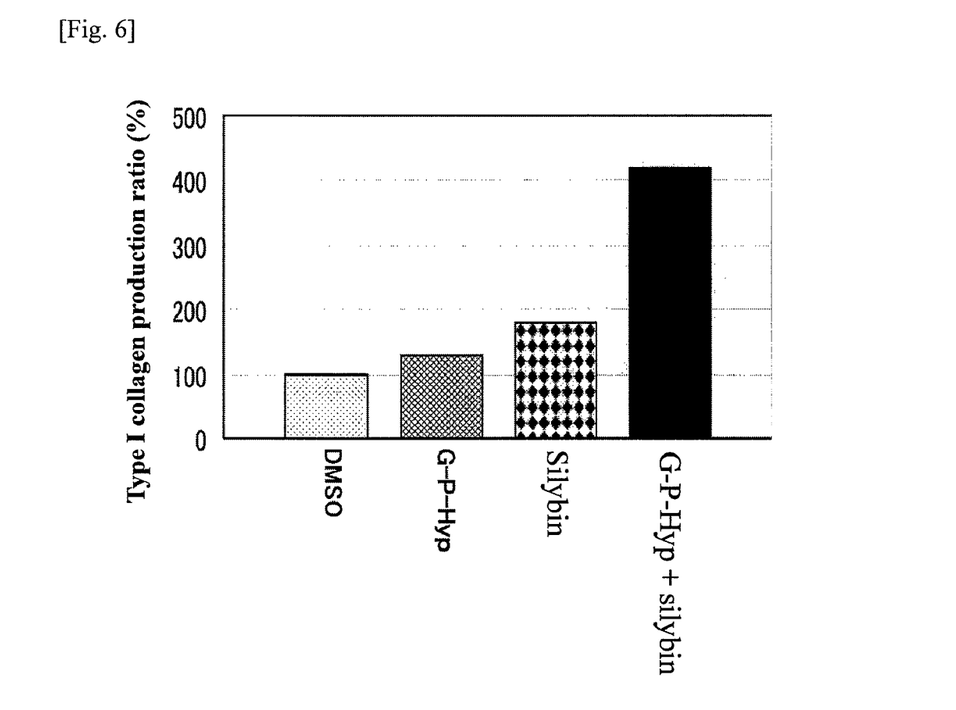
FIG. 6 A graph showing the numerical values of the results in FIG. 5, derived by conversion based on imaging analysis processing. Gly-Pro-Hyp is referred to as "G-P-Hyp."

When 30 µM of Gly-Pro-Hyp was used alone, 5 µM of silybin was used alone, and 30 µM of Gly-Pro-Hyp and 5 µM of silybin were used in combination, type I collagen production was 1.25 times, 1.85 times and 4.25 times, respectively, compared to the level in the control that was not given any treatment (FIGS. 5 and 6). Accordingly, it is clear that a combined use of Gly-Pro-Hyp and silybin promotes the production of type I collagen synergistically compared to when they are used alone.

Example 3

Figure 7:
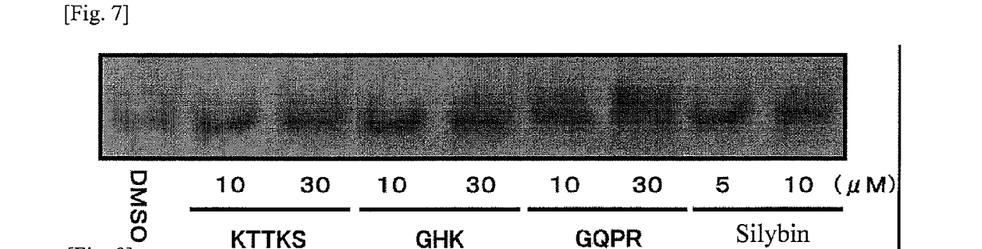
FIG. 7 A graph showing the detection results, by means of Western blotting, of the type I collagen production by peptides having a Lys-Thr-Thr-Lys-Ser (SEQ ID NO: 1, referred to as "K-T-T-K-S"), Gly-His-Lys (referred to as "G-H-K") or Gly-Glu-Pro-Arg (SEQ ID NO: 2, referred to as "G-Q-P-R") sequence and silybin in a three-dimensional human skin model.
Figure 8:
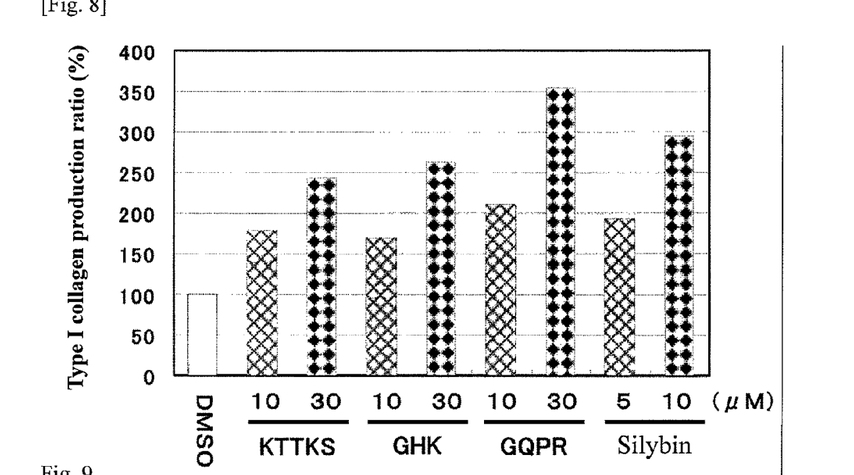
FIG. 8 A graph showing the numerical values of the results in FIG. 7, derived by conversion based on imaging analysis processing. Lys-Thr-Thr-Lys-Ser (SEQ ID NO: 1) is referred to as "K-T-T-K-S," Gly-His-Lys is referred to as "G-H-K," and Gly-Glu-Pro-Arg (SEQ ID NO: 2) is referred to as "G-Q-P-R."
Figure 9:
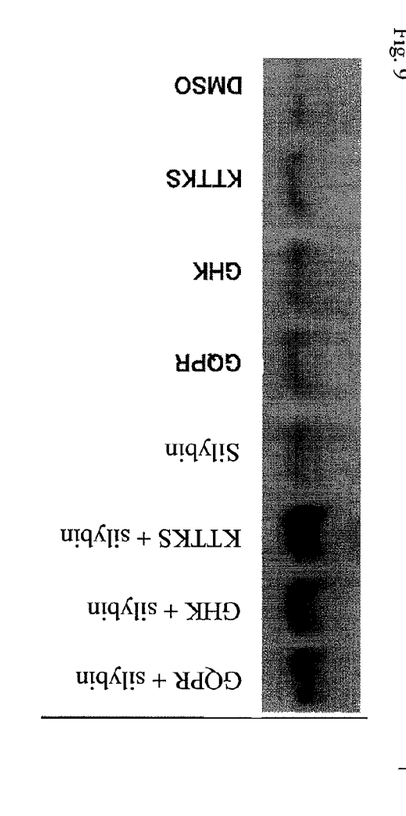
FIG. 9 A graph showing the detection results, by means of Western blotting, of the type I collagen production by peptides having a Lys-Thr-Thr-Lys-Ser (SEQ ID NO: 1, referred to as "K-T-T-K-S"), Gly-His-Lys (referred to as "G-H-K") or Gly-Glu-Pro-Arg (SEQ ID NO: 2, referred to as "G-Q-P-R") sequence, used in combination with silybin, in a three-dimensional human skin model.

Evaluation of Actions to Promote Type I Collagen Production from Use of Lys-Thr-Thr-Lys-Ser, Gly-His-Lys and Gly-Glu-Pro-Arg Alone and Combined Use of Lys-Thr-Thr-Lys-Ser, Gly-His-Lys and Gly-Glu-Pro-Arg with Silybin Three-dimensional human skin models were treated with Lys-Thr-Thr-Lys-Ser (SEQ ID NO: 1), Gly-His-Lys and Gly-Glu-Pro-Arg (SEQ ID NO: 2) at concentrations of 10 and 30 µM, respectively, and the amount of type I collagen was measured by means of Western blotting. FIG. 7 shows the detected bands, while FIG. 8 shows a graph indicating the numerical values of detected bands. Similarly, three-dimensional human skin models were treated with Lys-Thr-Thr-Lys-Ser, Gly-His-Lys and Gly-Glu-Pro-Arg alone at 10 µM each, with silybin alone at 5 µM, and with Lys-Thr-Thr-Lys- Ser (SEQ ID NO: 1), Gly-His-Lys and Gly-Glu-Pro-Arg (SEQ ID NO: 2) at 10 μM each in combination with silybin at 5 μM, and the amount of type I collagen was measured by means of Western blotting. FIG. 9 shows the detected bands, while FIG. 10 shows a graph indicating the numerical values of detected bands.

Treating with Lys-Thr-Thr-Lys-Ser, Gly-His-Lys (SEQ ID NO: 1) and Gly-Glu-Pro-Arg (SEQ ID NO: 2) at 10 and 30 μM, respectively, resulted in type I collagen production of 1.80 times and 2.45 times in the case of Lys-Thr-Thr-Lys-Ser (SEQ ID NO: 1) at 10 and 30 μM, respectively, 1.75 times and 2.70 times in the case of Gly-His-Lys at 10 and 30 μM, respectively, and 2.15 times and 3.55 times in the case of Gly-Glu-Pro-Arg (SEQ ID NO: 2) at 10 and 30 μM, respectively, compared to the level in the control that was not given any treatment (FIGS. 7 and 8). Accordingly, it is clear that Lys-Thr-Thr-Lys-Ser (SEQ ID NO: 1), Gly-His-Lys and Gly-Glu-Pro-Arg (SEQ ID NO: 2) all promote type I collagen production in a manner dependent on the concentration.

Figure 10:
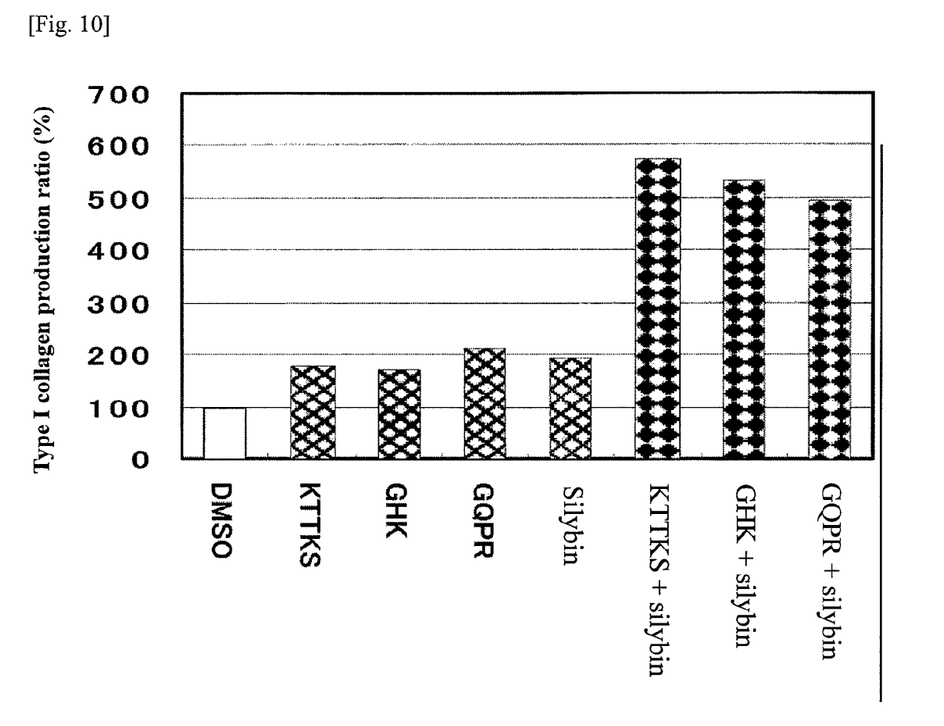
FIG. 10 A graph showing the numerical values of the results in FIG. 9, derived by conversion based on imaging analysis processing. Lys-Thr-Thr-Lys-Ser (SEQ ID NO: 1) is referred to as "K-T-T-K-S," Gly-His-Lys is referred to as "G-H-K," and Gly-Glu-Pro-Arg (SEQ ID NO: 2) is referred to as "G-Q-P-R.".

Also, treating with Lys-Thr-Thr-Lys-Ser (SEQ ID NO: 1), Gly-His-Lys and Gly-Glu-Pro-Arg (SEQ ID NO: 2) alone at 10 μM each, and with silybin alone at 5 μM, caused type I collagen production to increase to 1.80 times, 1.75 times, 2.10 times and 1.95 times, respectively, compared to the level in the control that was not given any treatment (FIGS. 9 and 10), while treating with Lys-Thr-Thr-Lys-Ser (SEQ ID NO: 1), Gly-His-Lys and Gly-Glu-Pro-Arg (SEQ ID NO: 2) at 10 μM each in combination with silybin at 5 μM further increased type I collagen production to 5.75 times, 5.35 times and 4.95 times, respectively, compared to the level in the control that was not given any treatment (FIGS. 9 and 10). Accordingly, it is clear that a combined use of Lys-Thr-Thr-Lys-Ser (SEQ ID NO: 1), Gly-His-Lys and Gly-Glu-Pro-Arg (SEQ ID NO: 2) with silybin promote the production of type I collagen synergistically compared to when they are used alone.

Examples of prescription under the present invention are provided below. It should be noted, however, that the present invention is not at all limited to these examples of prescription.

Example of Prescription 1 Manufacture of Capsules

The following ingredients were mixed and filled into capsules containing a mixture of gelatin and glycerin to obtain soft capsules.

| (Composition) | (Content: mg) |
|---|---|
| Milk thistle extract (containing 35% silybin) | 25 |
| Soybean extract (containing 80% soybean saponin) | 25 |
| Gly-Pro-Hyp (refined collagen decomposition product) | 25 |
| Tocotrienol | 30 |
| Bees wax | 10 |
| Grape seed oil | 110 |

Example of Prescription 2 Manufacture of Tablets

The following ingredients were mixed and compressed into a tablet shape to obtain tablets.

| (Composition) | (Content: mg) |
|---|---|
| Milk thistle extract (containing 35% silybin) | 25 |
| Soybean extract (containing 80% soybean saponin) | 25 |
| Gly-Pro-Hyp (refined collagen decomposition product) | 25 |
| Cellulose | 40 |
| Starch | 20 |
| Sucrose fatty acid ester | 2 |

Example of Prescription 3 Manufacture of Tablets

The following ingredients were mixed and compressed into a tablet shape to obtain tablets.

| (Composition) | (Content: mg) |
|---|---|
| Milk thistle extract (containing 35% silybin) | 25 |
| Soybean extract (containing 80% soybean saponin) | 25 |
| Lys-Thr-Thr-Lys-Ser (peptide) | 25 |
| Cellulose | 40 |
| Starch | 20 |
| Sucrose fatty acid ester | 2 |

Example of Prescription 4 Manufacture of Tablets

The following ingredients were mixed and compressed into a tablet shape to obtain tablets.

| (Composition) | (Content: mg) |
|---|---|
| Milk thistle extract (containing 35% silybin) | 25 |
| Soybean extract (containing 80% soybean saponin) | 25 |
| Gly-His-Lys (peptide) | 25 |
| Cellulose | 40 |
| Starch | 20 |
| Sucrose fatty acid ester | 2 |

Example of Prescription 5 Manufacture of Tablets

The following ingredients were mixed and compressed into a tablet shape to obtain tablets.

| (Composition) | (Content: mg) |
|---|---|
| Milk thistle extract (containing 35% silybin) | 25 |
| Soybean extract (containing 80% soybean saponin) | 25 |
| Gly-Glu-Pro-Arg (peptide, SEQ ID NO: 2) | 25 |
| Cellulose | 40 |
| Starch | 20 |
| Sucrose fatty acid ester | 2 |

Example of Prescription 6 Manufacture of Juice

| (Composition) | (Content: % by mass) |
|---|---|
| Fructose glucose liquid sugar | 5.00 |
| Citric acid | 10.40 |
| L-ascorbic acid | 0.20 |
| Aromatic agent | 0.02 |
| Colorant | 0.10 |
| Milk thistle extract (containing 35% silybin) | 1.00 |
| Gly-Glu-Pro-Arg (peptide, SEQ ID NO: 2) | 1.00 |
| Soybean extract (containing 80% soybean saponin) | 1.00 |
| Water | 81.28 |

Example of Prescription 7 Manufacture of Cream

Among the following ingredients, (1) through (12) were dissolved by heating to 80° C. to obtain an oil phase. Ingredients (13) through (15) were dissolved by heating to 70° C. to obtain a water phase. The water phase was gradually added to the oil phase to cause emulsification and the mixture was cooled to 40° C. under agitation, and then further cooled to 30° C. under agitation to obtain cream.

| (Composition) | (Content: % by mass) |
|---|---|
| (1) Stearyl alcohol | 6.0 |
| (2) Stearic acid | 2.0 |
| (3) Hydrogenated lanolin | 4.0 |
| (4) Squalane | 9.0 |
| (5) Octyl dodecanol | 10.0 |
| (6) POE (25) cetyl alcohol ether | 3.0 |
| (7) Glycerin monostearate | 2.0 |
| (8) *Bletilla striata* extract | 0.1 |
| (9) Milk thistle extract (containing 85% silybin) | 0.7 |
| (10) Gly-Pro-Hyp (refined collagen decomposition product) | 0.1 |
| (11) Preservative | As appropriate |
| (12) Aromatic agent | As appropriate |
| (13) 1,3-butylene glycol | 6.0 |
| (14) PEG 1500 | 4.0 |
| (15) Purified water | Remainder |

Example of Prescription 8 Manufacture of Cream

Among the following ingredients, (1) through (12) were dissolved by heating to 80° C. to obtain an oil phase. Ingredients (13) through (15) were dissolved by heating to 70° C. to obtain a water phase. The water phase was gradually added to the oil phase to cause emulsification and the mixture was cooled to 40° C. under agitation, and then further cooled to 30° C. under agitation to obtain cream.

| (Composition) | (Content: % by mass) |
|---|---|
| (1) Stearyl alcohol | 6.0 |
| (2) Stearic acid | 2.0 |
| (3) Hydrogenated lanolin | 4.0 |
| (4) Squalane | 9.0 |
| (5) Octyl dodecanol | 10.0 |
| (6) POE (25) cetyl alcohol ether | 3.0 |
| (7) Glycerin monostearate | 2.0 |
| (8) *Bletilla striata* extract | 0.1 |
| (9) Milk thistle extract (containing 85% silybin) | 0.7 |
| (10) Lys-Thr-Thr-Lys-Ser (peptide) | 0.1 |
| (11) Preservative | As appropriate |
| (12) Aromatic agent | As appropriate |
| (13) 1,3-butylene glycol | 6.0 |
| (14) PEG 1500 | 4.0 |
| (15) Purified water | Remainder |

Example of Prescription 9 Manufacture of Cream

Among the following ingredients, (1) through (12) were dissolved by heating to 80° C. to obtain an oil phase. Ingredients (13) through (15) were dissolved by heating to 70° C. to obtain a water phase. The water phase was gradually added to the oil phase to cause emulsification and the mixture was cooled to 40° C. under agitation, and then further cooled to 30° C. under agitation to obtain cream.

| (Composition) | (Content: % by mass) |
|---|---|
| (1) Stearyl alcohol | 6.0 |
| (2) Stearic acid | 2.0 |
| (3) Hydrogenated lanolin | 4.0 |
| (4) Squalane | 9.0 |
| (5) Octyl dodecanol | 10.0 |
| (6) POE (25) cetyl alcohol ether | 3.0 |
| (7) Glycerin monostearate | 2.0 |
| (8) *Bletilla striata* extract | 0.1 |
| (9) Milk thistle extract (containing 85% silybin) | 0.7 |
| (10) Gly-His-Lys (peptide) | 0.1 |
| (11) Preservative | As appropriate |
| (12) Aromatic agent | As appropriate |
| (13) 1,3-butylene glycol | 6.0 |
| (14) PEG 1500 | 4.0 |
| (15) Purified water | Remainder |

Example of Prescription 10 Manufacture of Cream

Among the following ingredients, (1) through (12) were dissolved by heating to 80° C. to obtain an oil phase. Ingredients (13) through (15) were dissolved by heating to 70° C. to obtain a water phase. The water phase was gradually added to the oil phase to cause emulsification and the mixture was cooled to 40° C. under agitation, and then further cooled to 30° C. under agitation to obtain cream.

| (Composition) | (Content: % by mass) |
|---|---|
| (1) Stearyl alcohol | 6.0 |
| (2) Stearic acid | 2.0 |
| (3) Hydrogenated lanolin | 4.0 |
| (4) Squalane | 9.0 |
| (5) Octyl dodecanol | 10.0 |
| (6) POE (25) cetyl alcohol ether | 3.0 |
| (7) Glycerin monostearate | 2.0 |
| (8) *Bletilla striata* extract | 0.1 |
| (9) Milk thistle extract (containing 85% silybin) | 0.7 |
| (10) Gly-Glu-Pro-Arg (peptide, SEQ ID NO: 2) | 0.1 |
| (11) Preservative | As appropriate |
| (12) Aromatic agent | As appropriate |
| (13) 1,3-butylene glycol | 6.0 |
| (14) PEG 1500 | 4.0 |
| (15) Purified water | Remainder |

What is claimed is:

1. A composition for promoting type I collagen production, characterized by containing silybin and a peptide that promotes collagen production, said peptide having the amino acid sequence of Gly-Pro-Hyp.

2. The composition according to claim 1, which is formulated for animals.

3. A cosmetic, characterized by containing silybin and a peptide having the amino acid sequence of Gly-Pro-Hyp.

4. The cosmetic according to claim 3, which is a topical cosmetic containing the silybin and the peptide at a mole ratio of 1:2 to 1:6 each in an amount of 0.01 to 2% by weight.

5. A composition for promoting type I collagen production comprising silybin and a peptide having the amino acid sequence of Gly-Pro-Hyp in an amount effective to promote type I collagen production in human skin fibroblasts.

6. The composition according to claim 5, wherein the silybin and the peptide are contained at a mole ratio of 1:2 to 1:6.

7. A food, characterized by containing silybin and a peptide having the amino acid sequence of Gly-Pro-Hyp.

8. The food according to claim 7, which contains the silybin and the peptide at a mole ratio of 1:2 to 1:6 each in an amount of 0.1 to 10% by weight.

* * * * *